United States Patent [19]

Ferguson

[11] Patent Number: 4,685,990
[45] Date of Patent: Aug. 11, 1987

[54] OSTOMY BAG COUPLING

[75] Inventor: Keith T. Ferguson, Scotch Plains, N.J.

[73] Assignee: E. R. Squibb & Sons, Inc., Princeton, N.J.

[21] Appl. No.: 912,716

[22] Filed: Sep. 29, 1986

Related U.S. Application Data

[62] Division of Ser. No. 759,560, Jul. 26, 1985, Pat. No. 4,648,875.

[51] Int. Cl.⁴ .................... B32B 31/00; B32B 31/20
[52] U.S. Cl. .................................. 156/253; 156/267; 156/292; 156/308.4
[58] Field of Search ............... 156/253, 267, 290, 292, 156/308.4, 309.6; 604/338–344, 332, 336, 337, 346, 355

[56] References Cited

U.S. PATENT DOCUMENTS 3,339,546  9/1967  Chen .
4,213,458  7/1980  Nolan et al. .
4,419,100  12/1983 Alexander ........................... 604/339
4,460,363  7/1984  Steer et al. .

FOREIGN PATENT DOCUMENTS 0094613  11/1983  European Pat. Off. .
0098718  1/1984   European Pat. Off. .
1274382  5/1972   United Kingdom .
1571657  7/1980   United Kingdom .

*Primary Examiner*—Donald E. Czaja
*Assistant Examiner*—Geoffrey L. Knable
*Attorney, Agent, or Firm*—Lawrence S. Levinson; Robert E. Lee, Jr.

[57] ABSTRACT

An ostomy device comprises an ostomy bag with a first coupling member attached thereto. A second coupling member for mating engagement with the first is attached to an adhesive backed label for adhering to the skin of the wearer around a stoma by a flexible mounting member comprising first and second sections coupled together at an inner peripheral region defining a stoma aperture therein. The second coupling member is attached to the first section at an outer peripheral region spaced apart from the inner peripheral region by hot melt adhesive while the second section is attached to the label at an outer peripheral region spaced apart from the inner peripheral region. The second section is attached by hot melt adhesive.

5 Claims, 6 Drawing Figures

OSTOMY BAG COUPLING

This is a division of application Ser. No. 759,560, filed July 26, 1985, now U.S. Pat. No. 4,648,875.

BACKGROUND OF THE INVENTION

The present invention relates to an ostomy bag and to an improved coupling for joining an ostomy bag to a pad, label or surgical dressing.

Ostomy bags are used to collect waste from patients with a stoma resulting from an ileostomy, colostomy or similar surgical procedure. An ostomy bag comprises two thin film walls which are sealed along their periphery by heat welding or the like. One wall has an aperture to receive the stoma.

The ostomy bag is secured to the patient by attaching it to an adhesive backed label through which an opening can be made in the center to receive the stoma. The adhesive backed label can be worn comfortably for extended periods of time which are longer than the time normally required for the bag to fill to capacity with waste material. Examples of acceptable adhesive backed labels are described in U.S. Pat. No. 3,339,546 by Chen.

It is desirable when replacing the filled ostomy bag with an empty one that the ostomy bag be removed and replaced without requiring that the adhesive backed label be removed. This is accomplished through the use of a coupler which comprises a pair of plastic rings, one of which forms a channel or groove and the other, a projection or rib for frictional engagement with the channel or groove. Each ring defines an aperture for receiving a stoma therethrough. One ring, usually the one with the channel, is attached to the bag with its aperture aligned with the aperature in the bag, while the other ring is attached to the label on a surface opposite the adhesive, also with its aperture aligned with the opening in the bag when the two rings are coupled together. Using this coupling arrangement the bag and label can be connected around the stoma by aligning the coupler rings and pressing them together to cause frictional engagement. A coupler suitable for this application is described in Great Britain Patent specification No. 1,571,657, published July 16, 1980.

The coupling rings are coupled together by applying a significant force on the bag to press the rings together. Where one of the coupling rings is mounted directly to the surface of the label, a great amount of the force is absorbed by the sensitive skin beneath the label. In the prior art to reduce the force applied to the skin, an outwardly extending flange portion of the ring to be attached to the label is attached along a portion of its bottom surface to an outer edge portion of a thin annular web of flexible thermoplastic material. The web extends inwardly from the flange portion and the inner edge portion of the web is attached to the label. This arrangement allows a user of the ostomy bag to insert the user's fingers between the web and the label and press the coupling rings together to attach the ostomy bag to the label. The fingers then absorb at least some of the applied force. See U.S. Pat. No. 4,419,100. This patent further discloses that the inner edge of the web may be attached to an annular mounting collar which in turn is attached to the faceplate to reinforce it in the area about the opening which receives the stoma.

In European Patent application No. AI0098718 published Jan. 18, 1984, a ring mounting means for mounting a coupling ring to the label is disclosed which includes a first section adapted to be affixed to the surface of the label and an accordion-like section positioned between the first section and a second section to be attached to the coupling ring. The accordion-like sections facilitate further displacement of the coupling ring from the label over the single web of thermoplastic material described above so that the coupling rings can be engaged and the forces diverted from the skin around the stoma by permitting the mounting means to expand when the fingers are inserted between the coupling ring and the label. Accordion-like sections with a single fold and triple folds are explicitly disclosed. The single fold is higher to provide the same amount of movement away from the label as the triple fold design without moving the mounting ring away from the attachment but has the disadvantage of providing a higher profile. Also, the single fold design places more stress on the single hinge at the fold sometimes resulting in cracking at the fold.

When designing the mounting means for attaching a coupling ring such as the coupling rings described above it is desirable to provide maximum flexibility, low profile, and comfort of use, while insuring adequate support for the ostomy bag during use and secure and reliable attachment of the mounting means to the label. At the same time it is desirable to maximize the area of the opening defined by attachment of the mounting means to the label for receiving the largest size stoma possible.

SUMMARY OF THE INVENTION

According to the present invention, an ostomy device is disclosed in which a flexible mounting member is employed to attach a coupling member to an adhesive backed label which is to be applied to the skin of the wearer around a stoma. An ostomy bag is equipped with its own coupling member for mating engagement with the coupling member attached to the label. The flexible mounting member comprises first and second sections coupled together at an inner peripheral region which defines a stoma aperture therein. The first section is attached to the coupling member while the second section is attached to the label along an outer peripheral region spaced apart from the inner periphery whereby the coupling member can be moved to a location spaced apart from the label.

In the preferred embodiment the mounting member is a polymeric foam such as polyethylene foam which is flexible enough to curve around the ends of the wearer's thumbs or fingers when they are placed between the first and second sections to couple or decouple the bag from the label.

To form the mounting member two sheets of polymeric foam are heat welded together along a closed loop region. A stoma aperture is cut out from both sheets within and adjacent the closed loop region. The excess material is trimmed off to form a boarder around the closed loop region thereby creating the first and second sections.

The coupling member is attached to the first section along an outer peripheral region by hot melt adhesive. Similarly, the second section is attached to the label by hot melt adhesive.

DETAILED DESCRIPTION OF THE DRAWINGS

Figure 1:
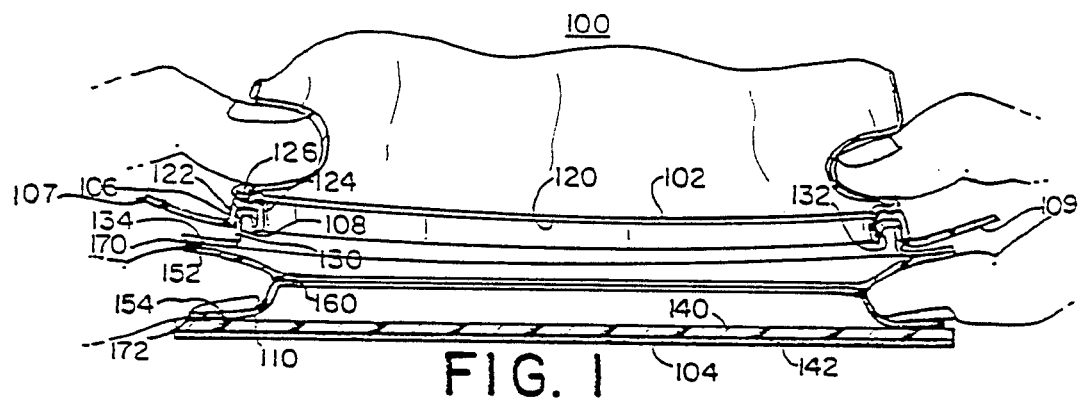
FIG. 1 is a partial cross-sectional view of one embodiment of the present invention ostomy device shown in an expanded positon.
Figure 2:
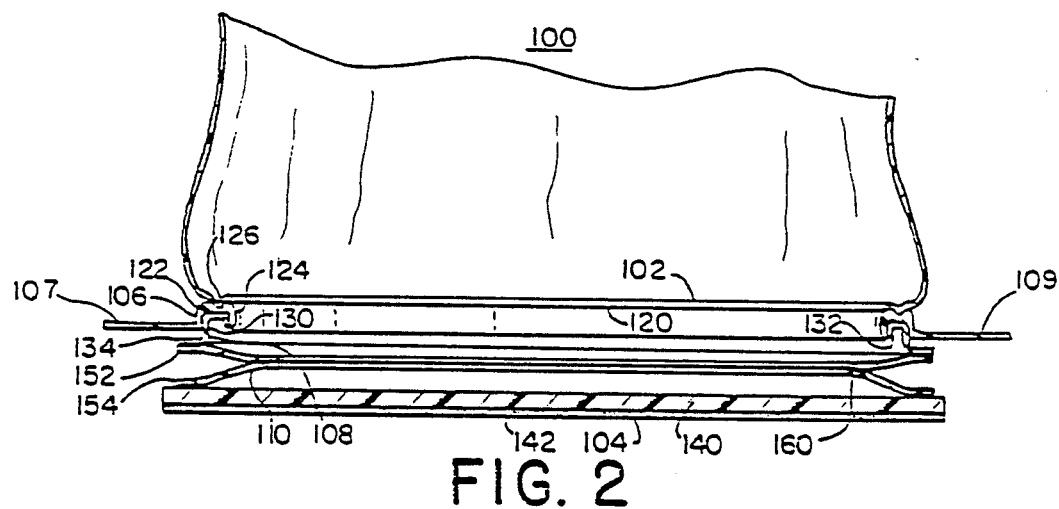
FIG. 2 is a cross-sectional view of the ostomy device of FIG. 1 shown in a normal position for use.

FIGS. 1 and 2 illustrate an ostomy device designated generally 100 of the present invention comprising an ostomy bag 102, an adhesive backed label 104 suitable for use on a patient's skin, first and second coupling rings 106 and 108 shown in frictional engagement, and a mounting means 110 for mounting one of the first or second rings 106 or 108, respectively, to the label 104. The mounting means, coupling rings and label are shown partially in cross-section. The first coupling ring 106 is shown attached to ostomy bag 102. Ostomy bag 102 has an aperture 120 therein to receive a stoma and coupling ring 106 is circular also defining an aperture. Ring 106 is positioned such that the aperture it defines is aligned with the bag aperture 120 to receive the stoma. Coupling ring 106 is preferably a deformable but resilient plastic material and comprises a channel formed by opposing walls 122 and 124 integrally connected together by base 126. The base 126 of coupling ring 106 is secured to the bag by adhesive or heat welding for example. Ring 106 further comprises tabs 107 and 109 which extend outwardly from the ring 106. They are shown only in cross section in FIG. 1 and form no part of the present invention.

Second coupling ring 108, also preferably made from a resilient and deformable plastic material and circular in shape to define an aperture comprises a rib portion 130, a deflectible sealing stip 132 and a flexible flange 134. The coupling members are adapted to be frictionally engaged by pressing them together, the rib portion 130 into the channel of the opposing coupling ring. When so engaged, the deflectible sealing strip 132 engages the surface of the wall and the aperture defined by ring 108 is aligned with the apertures of ring 106 and bag 102.

Either or both of coupling rings 106 and 108 may be injection molded from any suitable synthetic plastics material which may but need not be of low density polyethylene.

The purpose of the adhesive backed label 104 is to attach the ostomy device 100 to the skin of the wearer. Label 104 comprises a base 140 which is preferably a thin film of polymeric material such as polyethylene and an adhesive layer 142 situated on the rear surface of base 140. Adhesive layer 142 is preferably formed as a homogeneous blend of one or more pressure-sensitive viscous or elastomeric materials having intermittently dispersed therein one or more water-soluble or swellable hydrocolloid gums and may also include one or more thermoplastic elastomers and/or one of more swellable-cohesive strengthening agents.

The second coupling ring 108 is attached or mounted to the thin film of polymeric material of base 140 of label 104 by member 110 which comprises first and second sections 152 and 154, respectively, which are heat welded together at an inner periphery 160 of both sections to form an expandable V shaped member. The bottom surface of the outer periphery of flange 134 is attached to the outer periphery of the top surface of the first section 152 at 170 while the bottom surface of the outer periphery of the second section 154 is attached to the base 140 at 172. FIG. 1 shows the thumbs of the wearer inserted between the first and second sections and the fingers pressing on tabs 107 and 109 to couple the rings 106 and 108 together. The fingers could be placed behind the bag 102 pressing against the base 126 of coupling 106 instead of using the tabs. In FIG. 2, the coupling rings are shown coupled in the normal position for use by the wearer.

The mounting member 110 is made from a polymeric foam, preferably a polymeric closed cell foam such as polyethylene foam. The polyethylene foam provides greater flexibility and softness over the prior art relatively stiffer thermoplastic sheet materials.

A separate mounting member, here as well as in the prior art, is designed to provide flexibility and ease of use when coupling the ostomy bag to the label and for reducing or eliminating pain caused by pressing against the skin around the stoma. At the same time it is desireable to maximize the stoma aperture region within the label for a given coupling ring diameter. This is particularly true for loopostomies. The use of a flexible mounting member to accomplish the first objective often results in reducing the amount of useable stoma aperture in the label.

With the present invention design and using the polymeric foam material it is possible, as FIG. 1 shows, to insert the thumbs (or fingers) deeply into the V to contact the region 160 where the first and second sections are joined. The polymeric foam is so pliant that it forms around the curvature of the end of the thumb to allow the thumbs to be placed directly under the coupling ring. Because the second section is only attached along a portion of it bottom surface on the outer periphery to the base 140, it will lift from the base to form around the thumb. Mounting members made from polymeric plastic such as polyethylene, not a foam, do not have this property and will not allow a finger or thumb to be placed fully into the V but instead pinch the thumb or finger or prevent deeper penetration, therefore, forcing the coupling ring to be placed farther from the stoma aperture region.

In addition to the above, the polymeric foam has a softer feel or touch and is less abrasive to the stoma itself.

Figure 3:
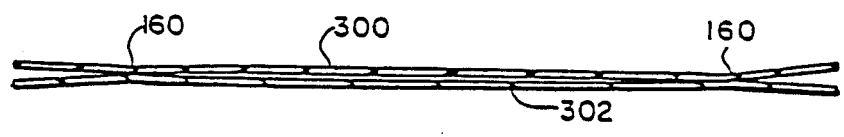
FIG. 3 is a cross-sectional view depicting a first step in forming the mounting member.
Figure 4:
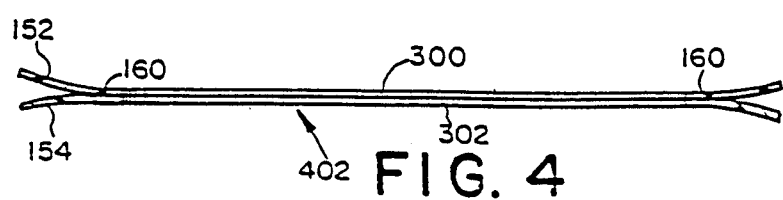
FIG. 4 is a partial cross-sectional view depicting a second step in forming the mounting member.
Figure 5:
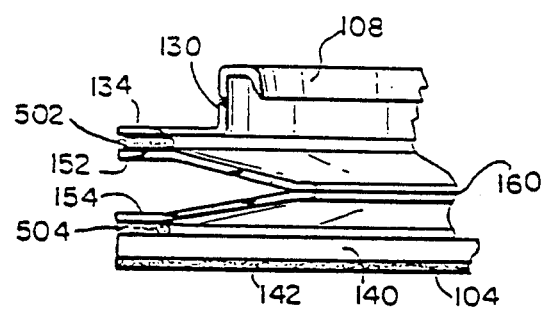
FIG. 5 is an exploded cross-sectional view of a portion of the ostomy device of FIGS. 1 and 2.

Referring now to FIGS. 3, 4 and 5 a method for making the improved coupling is described. In FIG. 3, two planer sheets of polyethylene foam 300 and 302, approximately 6 lbs. per cubic foot and 32 mils thick, are placed together and heat welded along a circular (or oval) region 160. Next a circular (or oval etc.) aperture 402 is cut out in both sheets with a perimeter adjacent the inner periphery of the welded region 160. The outer region of the sheets is trimmed away spaced apart from the outer periphery of region 160 leaving a border therearound to form a mounting member with the first and second sections 152 and 154 joined along a common inner periphery 160. In the preferred embodiment, the mounting member is in the shape of two annular rings, each about one half inch in width.

Next, as shown in FIG. 5, hot melt adhesive 502 is applied to either the outer region of the upper surface of first section 152 or the outer region of the bottom surface of flange 134. The outer region of the bottom of flange 134 of the coupling ring 108 is then attached to the first section 152 by the hot melt adhesive. Note, in the preferred embodiment, from FIG. 1, that the flange 134 is not attached to the first section 152 along its entire length but only along its outer periphery. This allows the coupling ring to lift away from the first section under the rib portion 130 providing greater flexibility.

Figure 6:
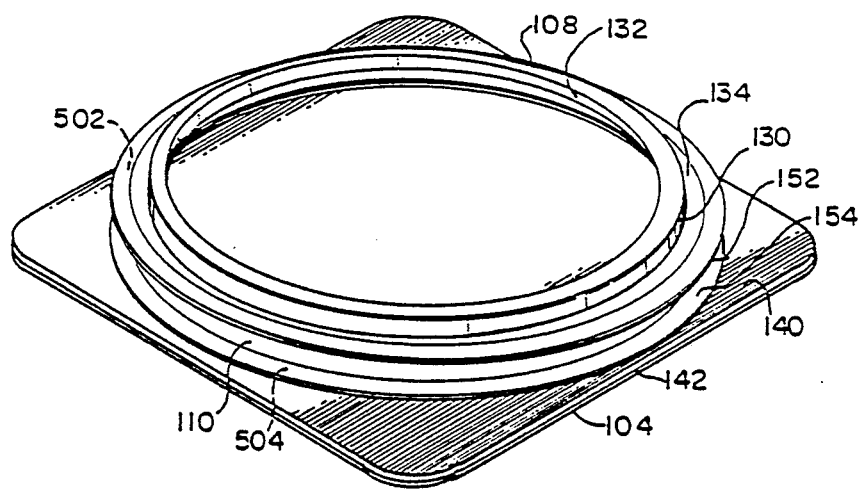
FIG. 6 is a perspective view of the preferred embodiment mounting member shown with a body side portion of the ostomy device.

In the final step of the assembly of the ostomy appliance, hot melt adhesive 504 is applied to either the outer portion of the bottom of the second section 154 or to a region on the layer 140 of label 104. The mounting member 110 with coupling ring 108 is then attached to the label by the hot melt adhesive. Of course, other suitable means such as heat welding, adhesives etc. can be used in place of hot melt adhesive for attaching the coupling ring to the mounting member and the mounting member to the label but hot melt adhesive has been found to be the most convenient. FIG. 6 shows the completed mounting member 110 with coupling ring 108 and label 104 attached.

What is claimed is:

1. A method of mounting a plastic coupling member to a surface of an adhesive backed label, said coupling member used for detachably connecting an ostomy bag to said label, said method comprising the steps of:
   providing a plastic coupling member and an adhesive backed label;
   forming a flexible mounting member comprising first and second sections coupled together at an inner peripheral region which defines an aperture therein and each said section having an outer peripheral region spaced from said inner peripheral region;
   coupling said plastic coupling member to said first section only at the outer peripheral region thereof;
   coupling said second section to a surface of said adhesive backed label only at the outer peripheral region of said second section so that said second section is movable away from said label in the region of the aperture.

2. The method of claim 1 wherein said flexible mounting member comprises polymeric foam.

3. The method of claim 2 wherein said polymeric foam comprises polyethylene foam.

4. The method of claim 2 wherein the step of forming further comprises:
   joining two sheets of said polymeric foam together along a closed loop region;
   forming said aperture in said two sheets having a perimeter adjacent said closed loop region; and
   trimming away excess material to form a border around said closed loop region to form said first and second sections.

5. The method of claim 4 wherein said coupling steps comprise applying hot melt adhesive between the surfaces of the portions to be coupled.

* * * * *